United States Patent [19]

Fiard et al.

[11] Patent Number: 5,362,707

[45] Date of Patent: * Nov. 8, 1994

[54] PLANT-PROTECTION SUSPO-EMULSIONS COMPRISING SUCROGLYCERIDES

[75] Inventors: Jean-Francois Fiard, Paris; Jean-Michel Mercier, Thiais; Marie-Luce Prevotat, Paris, all of France

[73] Assignee: Rhone-Poulenc Chimie, Courbevoie, France

[ * ] Notice: The portion of the term of this patent subsequent to Mar. 1, 2011 has been disclaimed.

[21] Appl. No.: 804,327

[22] Filed: Dec. 10, 1991

[30] Foreign Application Priority Data

Dec. 10, 1990 [FR] France .................................. 90 15739

[51] Int. Cl.$^5$ ............................................. A01N 25/30
[52] U.S. Cl. ..................................... 504/234; 504/265; 504/304; 504/330; 504/339; 504/347; 504/385; 514/245; 514/423; 514/471; 514/521; 514/755; 514/786; 71/DIG. 1
[58] Field of Search ...................... 71/93, 120, DIG. 1; 514/393, 412, 469, 521, 755, 786, 245, 423, 471; 504/116, 234, 265, 304, 330, 339, 347, 385; A01N 25/30

[56] References Cited

U.S. PATENT DOCUMENTS

| | | | |
|---|---|---|---|
| 3,882,243 | 5/1975 | Maeda et al. | 424/312 |
| 4,061,770 | 12/1977 | Marks | 71/DIG. 1 |
| 4,692,187 | 9/1987 | Kiehs et al. | 71/120 |

FOREIGN PATENT DOCUMENTS

| | | |
|---|---|---|
| 91331 | 10/1983 | European Pat. Off. . |
| 261492 | 3/1988 | European Pat. Off. . |
| 0373837 | 6/1990 | European Pat. Off. . |
| 2241667 | 3/1973 | Germany . |
| 423442 | 4/1967 | Switzerland . |
| 432442 | 4/1967 | Switzerland . |
| 2123294 | 2/1984 | United Kingdom . |

OTHER PUBLICATIONS

Mulqueen, Patrick J. et al. "Recent Development in Suspoemulsions Pesticide Science", *Pesticide Science* vol. 29, No. 4. pp.451–465, 1990.

*Primary Examiner*—Richard L. Raymond
*Assistant Examiner*—S. Mark Clardy
*Attorney, Agent, or Firm*—Finnegan, Henderson, Farabow, Garrett & Dunner

[57] ABSTRACT

The present invention relates to new plant-protection suspo-emulsions. More specifically, the invention relates to a suspo-emulsion of a solid active substance, having a melting point greater than or equal to 45° C. and which is substantially insoluble in water. The suspo-emulsion comprises at least one oil; a first surface-active system comprising at least sucroglycerides; the solid active substance; and either (A) a nonionic or anionic surface-active agent, or (B) a second surface-active system containing sucroglycerides and at least one compound selected from the group consisting of an alkoxylated triglyceride, an alkoxylated fatty acid, a sorbitan ester, and an alkoxylated sorbitan ester, and optionally a phospholipid.

52 Claims, No Drawings

PLANT-PROTECTION SUSPO-EMULSIONS COMPRISING SUCROGLYCERIDES

This application is related to copending application Ser. No. 07/804,322, filed Dec. 9, 1991, now U.S. Pat. No. 5,290,751, and Ser. No. 07/820,416, filed Jan. 15, 1992.

The present invention relates to new plant-protection suspo-emulsions. Active substances such as insecticides, germicides, herbicides, fungicides, acaricides, nematicides, molluscicides, rodenticides, attractants, repellents and combinations of these compounds, are generally insoluble in water. They can normally be used in solutions with organic solvents, wherein these solutions are emulsified in water at the time of their use. However, the use of solvents, such as xylenes or kerosene, presents obvious problems of environmental pollution.

Another mode of preparation of compositions of active substances consists of fluid aqueous dispersions, or "flowable" dispersions, which are diluted at the time of their use. These aqueous dispersions contain one or more surface-active agents.

Increasingly, more serious consideration is being given to the various problems of environmental pollution. Plant-protection compositions which are less and less toxic are being sought.

The present invention provides an alternative to environmentally harmful plant-protection suspensions through the use of a surface-active system which comprises, at least in part, non-toxic, non-irritant and biodegradable compounds. The emulsive and dispersive nature of sucroglycerides is known for preparing dispersed aqueous systems of fatty substances. Sucroglycerides are mixtures of products obtained by transesterification of natural or synthetic triglyceride with sucrose. These mixtures include monoglycerides, diglycerides, small quantities of nontransesterified triglycerides, monoesters and diesters of sucrose.

European patent application EP-A-0,091,331, which describes a process for the preparation of flowable sucroglycerides, also discloses that sucroglycerides have surface-active properties, which may be used especially for the preparation of emulsions of essential oils or of recombined milk. Sucroglycerides may also be combined with lecithins and flowable oils.

Swiss patent CH 423,442 describes a process for the preparation of emulsions of oils or solid fatty substances in water, using sucroglycerides and a lecithin as an emulsifying system.

The present invention uses the emulsive and/or dispersive ability of sucroglycerides for obtaining suspo-emulsions of active plant-protection substances. More specifically, the present invention relates to a suspo-emulsion of a solid active substance, having a melting point greater than or equal to 45° C., and being substantially insoluble in water. The suspo-emulsion comprises at least one oil; a first surface-active system containing at least sucroglycerides; the active substance; and either (A) a nonionic or anionic surface-active agent, or (B) a second surface-active system containing sucroglycerides, and at least one compound selected from an alkoxylated triglyceride, an alkoxylated fatty acid, a sorbitan ester and an alkoxylated sorbitan ester.

The suspo-emulsion in accordance with the present invention can be obtained by mixing its various constituent compounds. However, in order to further optimize the desired properties, such as the size of the particles in emulsion and the size of the particles in suspension, the suspo-emulsion is preferably prepared from a suspension of the active substance and an oil emulsion.

The suspo-emulsion of the present invention comprises a solid active substance, having a melting point greater than or equal to 45° C., which is substantially insoluble in water. The suspo-emulsion is preferably obtained by mixing an aqueous emulsion of at least one oil and a first surface-active system containing at least sucroglycerides, with an aqueous suspension of the active substance and either (A) a nonionic or anionic surface-active agent, or (B) a second surface-active system containing sucroglycerides and at least one compound selected from an alkoxylated triglyceride, an alkoxylated fatty acid, a sorbitan ester and an alkoxylated sorbitan ester.

The aqueous suspension, used for preparing the suspo-emulsion in accordance with the present invention, preferably contains a wetting agent in its surface-active system. Alkoxylated triglycerides can fulfill the role of the wetting agent, particularly for suspensions with low concentrations of active substance.

The aqueous emulsion employed in the present invention is preferably a direct emulsion (oil-in-water).

As previously indicated, sucroglycerides are obtained from the transesterification of triglycerides with sucrose. In the present text, the term "sucroglycerides" is used in the plural to indicate that they are not composed of only one chemical compound. The triglycerides of saturated or unsaturated aliphatic acids with at least 4 carbon atoms are preferably used. Preferably, the acids from which the triglycerides are derived contain 10 to 20 carbon atoms.

The preparation of sucroglycerides may be carried out using synthetic triglycerides, obtained by the reaction of glycerol and fatty acids. However, it is more useful from an economic point of view to use natural triglycerides. These natural triglycerides are mixtures of triglycerides.

Examples of natural triglycerides are lard, tallow, groundnut oil, butter oil, cotton-seed oil, linseed oil, olive oil, palm oil, grape-seed oil, fish oil, soybean oil, castor oil, colza oil, copra oil and coconut oil.

In the present invention, the sucroglycerides used are preferably obtained from palm oil, lard, copra oil, tallow, colza oil and castor oil. They are either in liquid form such as sucroglycerides of colza oil or castor oil, or in the form of more or less thick pastes, which are distinguishable notably by their melting point:

sucroglycerides of lard: 47° to 50° C.,
sucroglycerides of tallow: 50° to 55° C.,
sucroglycerides of palm oil: 55° to 58° C.,
sucroglycerides of copra oil: 60° to 62° C.

A method of preparation of sucroglycerides is described in French patent 2,463,512.

The aqueous emulsion used in the composition of the suspo-emulsion may also contain a phospholipid in combination with the sucroglycerides. Examples of phospholipids are crude lecithins of plant or animal origin, such as soybean lecithin or egg-yolk lecithin, as well as any lecithin fraction.

The oil may be natural triglycerides, and alkyl esters having 1 to 4 carbon atoms of the fatty acids used in the composition of natural triglycerides which are liquid at room temperature, for example 20° C. Non-restrictive examples of the oil are colza oil, sunflower oil, palm oil, groundnut oil, linseed oil, copra oil, grape-seed oil, nut oil, fish oil and methyl oleate. Preferably, for economic reasons, colza oil, sunflower oil, soybean oil and methyl oleate are used.

The aqueous emulsion, which is used in the composition of the suspo-emulsions in accordance with the invention, preferably contains, by weight relative to the total volume of the emulsion:
from 0.2% to 15% of sucroglycerides,
from 0% to 8% of phospholipid,
from 5% to 70% of oil,
and completed to 100% with water.

The composition by weight of the aqueous emulsion is more preferably the following:
from 0.5% to 10% of sucroglycerides,
from 0% to 5% of phospholipid,
from 10% to 60% of oil,
and completed to 100% with water.

The emulsion may also contain at least one compound selected from alkoxylated triglycerides, alkoxylated fatty acids, sorbitan esters and alkoxylated sorbitan esters, and preferably selected from ethoxylated triglycerides, ethoxylated fatty acids, sorbitan esters and ethoxylated sorbitan esters.

The ethoxylated triglycerides may be ethoxylated triglycerides of plant or animal origin such as lard, tallow, groundnut oil, butter oil, cotton-seed oil, linseed oil, olive oil, palm oil, grape-seed oil, fish oil, soybean oil, castor oil, colza oil, copra oil and coconut oil.

The ethoxylated fatty acids are preferably ethoxylated esters of fatty acids such as oleic acid or stearic acid.

The sorbitan esters are preferably cyclic sorbitol esters of from $C_{10}$ to $C_{20}$ fatty acids such as lauric acid, stearic acid or oleic acid. These sorbitan esters may also be ethoxylated.

The term ethoxylated triglyceride, in the present invention, applies to products obtained by ethoxylation of a triglyceride with ethylene oxide as well as to those obtained by transesterification of a triglyceride with a polyethylene glycol.

Similarly, the term ethoxylated fatty acid includes products obtained by ethoxylation of a fatty acid with ethylene oxide as well as those obtained by esterification of a fatty acid with polyethylene glycol.

The alkoxylated triglycerides, alkoxylated fatty acids, sorbitan esters, and/or alkoxylated sorbitan esters preferably represent from 0 to 10% by weight per volume of the emulsion and, more preferably, from 0.2% to 6% by weight per volume.

The aqueous emulsions used to prepare the suspo-emulsions in LAW accordance with the invention possess a very good physico-chemical stability and good compatibility with a large number of suspensions of active substances.

The active plant-protection substance used in the present invention is substantially insoluble in water, preferably its solubility in water at 20° C. is lower than 5 g/liter. Furthermore, the active substances used must be stable with respect to water.

Non-restrictive examples of active substances which can be used in the suspo-emulsions in accordance with the present invention are deltamethrin, propham, tetramethrin, furalaxyl, heptachlor, propanil, oxadiazon, triflumizole, dimethamethrin, atrazine, diuron, neburon, linuron, isoproturon, simazine, ametryne, phenmedipham, and pendimethalin.

The sucroglycerides, which may be used in the composition of the second surface-active system of suspensions of active substance, are as previously defined for the emulsions. The sucroglycerides may be combined with a phospholipid, as previously defined, but the use of a phospholipid is not critical to the suspension of active substance.

In the second surface-active system based on sucroglycerides, used in the suspension, the weight ratio of phospholipid to sucroglycerides is generally 0 to 3.

The second surface-active system based on sucroglycerides, which may be used to prepare the suspension of active substance, also contains at least one compound selected from alkoxylated triglyceride, an alkoxylated fatty acid, a sorbitan ester and an alkoxylated sorbitan ester. More particularly, the surface-active system contains the ethoxylated triglycerides, ethoxylated fatty acids, sorbitan esters and ethoxylated sorbitan esters which have been previously described.

The alkoxylated triglycerides, alkoxylated fatty acids, sorbitan esters and alkoxylated sorbitan esters generally represent from 0.1% to 3% by weight per volume of the suspension and preferably from 0.2% to 2.8% by weight/volume.

The second surface-active system based on sucroglycerides, which may be used to prepare the suspension of active substance, preferably contains at least one wetting agent.

The wetting agent is a compound as defined in the standard NF T 73/000. Examples of wetting agents are the anionic salts of surface-active agents, alkoxylated alcohols or alkoxylated alkylphenols represented by the following formulae:

$R_1\text{-}SO_3\text{-}M$ $R_2\text{-}SO_4\text{-}M$ $R_3\text{-}(EO)_n\text{-}H$ $R_3\text{-}(PO)_n\text{-}H$ $R_3\text{-}(EO\text{-}PO)_n\text{-}H$ $R_4\text{-}COONa$ where:
$R_1$ represents
an alkylphenyl radical such as dodecylphenyl,
an alkyl radical such as dodecyl, or
a 1,2-bis(octyloxycarbonyl) ethyl, preferably 1,2-bis(2-ethylhexyloxycarbonyl) ethyl,
$R_2$ represents
an alkyl radical such as dodecyl,
an ethoxylated alkylphenol radical such as ethoxylated nonylphenol with 2 to 50 EO units, or
an ethoxylated alkyl radical,
$R_3$ represents
an alkylaryl radical such as nonylphenyl or alkylnaphthyl, or
an alkyl radical having 8 to 20 carbon atoms, preferably from 10 to 14 carbon atoms,
n is a number from 4 to 12,
$R_4$ represents an alkyl radical having 10 to 22 carbon atoms,
M represents Na, K, $NH_4$ or a triethanolammonium cation.

The wetting agent may also be a silicone-based surface-active agent such as a copolymer of (1) polydimethylsiloxane and (2) either a homopolymer of ethylene glycol or a copolymer of ethylene glycol and propylene glycol. The wetting agent may also be a fluorinated surface-active agent such as a compound containing a hydrophobic or oleophobic perfluorocarbon linear chain and a hydrophilic region containing, for example, an acidic or neutralized sulphonic group, a carboxylic group or an ethoxylated alcohol radical.

The suspensions generally contain from 0.05% to 1% by weight of wetting agent relative to the total volume of the LAW suspension, and preferably from 0.1% to 0.8% by weight/volume.

The nonionic surface-active agent, which may be used to prepare the suspension of active substance, may be selected from alkoxylated di(1-phenylethyl) phenols, alkoxylated tri(1-phenylethyl)phenols, alkoxylated alkylphenols, alkoxylated fatty amines, alkoxylated fatty alcohols, and block polymers of ethylene oxide-propylene oxide-ethylene oxide (EO-PO-EO).

The alkoxylated units of these surface-active agents are oxyethylene and/or oxypropylene units. Their number usually varies from 2 to 100 depending on the HLB (hydrophilic/lipophilic balance) desired. Preferably, the number of alkoxylated units is between 4 and 50.

Alkoxylated alkylphenols generally have 1 or 2 linear or branched alkyl groups having 4 to 12 carbon atoms, particularly octyls, nonyls or dodecyls. The alkoxylated fatty amines preferably have from 10 to 22 carbon atoms. The alkoxylated fatty alcohols preferably have from 6 to 22 carbon atoms.

Examples of nonionic surface-active agents are ethoxylated di(1-phenylethyl)phenol with 15 ethylene oxide (EO) units, ethoxylated tri(1-phenylethyl)phenol with 16 EO units, ethoxylated tri(1-phenylethyl)phenol with 25 EO units, ethoxylated tri(1-phenylethyl)phenol with 40 EO units, ethoxypropoxylated tri(1-phenylethyl)phenols, ethoxypropoxylated nonylphenols, and trisequenced polymers EO-PO-EO.

The anionic surface-active agent which may be used to prepare the suspension of active substance is preferably selected from phosphoric esters of ethoxylated alkylphenols, ethoxylated di(1-phenylethyl)phenols, ethoxylated tri(1-phenyl-ethyl)phenols, ethoxylated fatty alcohols; sulphuric esters of ethoxylated alkylphenols, ethoxylated di(1-phenylethyl)phenols, ethoxylated tri(1-phenylethyl)phenols, ethoxylated fatty alcohols; sulphonic esters of ethoxylated alkylphenols, ethoxylated di(1-phenylethyl)phenols, ethoxylated tri(1-phenylethyl)phenols; the salts of polycarboxylic acids, the homo- and copolymers of polycarboxylic acids (such as polyacrylic and polymethacrylic acids), copolymers of maleic anhydride and diisobutylene; alkylnaphthalenesulphonates, poly(alkylnaphthaleneulphonates); and dihydroxydiphenylsulphonates condensed with formaldehyde.

Examples of anionic surface-active agents are triethanolamine salts of mono- and diphosphoric esters of ethoxylated tri(1-phenylethyl)phenol with 16 EO units, the ethoxylated acid sulphate of di(1-phenylethyl)phenol with 11 EO units, the ethoxylated acid phosphate of nonylphenol with 9 EO units, sodium methylnaphthalenesulphonate, and the sodium salt of polyacrylic acid. Mixtures of nonionic surface-active agents and/or of anionic surface-active agents may be used.

The aqueous suspension of the active substance preferably contains from 5% to 90% by weight of active substance, relative to the total volume of the suspension, and more preferably from 10 to 85% by weight/volume. The aqueous suspension may comprise from 0.2% to 15% by weight/volume of a nonionic or anionic surface-active agent and preferably from 0.5% to 10% by weight/volume. Alternatively, the aqueous suspension may comprise 0.1% to 5% by weight of sucroglyceride and phospholipid, preferably from 0.2% to 4%, 0.1% to 3% by weight of at least one selected from alkoxylated triglycertde, alkoxylated fatty acid, sorbitan ester and alkoxylated sorbitan ester as previously defined, preferably from 0.2% to 2.8%, and from 0.05% to 1% by weight of wetting agent, preferably from 0.1% to 0.8%, relative to the total volume of the aqueous suspension.

The suspo-emulsions according to the present invention may contain, in addition to the compounds previously defined, other normal constituents of plant-protection compositions, for example, antifoaming agents such as organopolysiloxanes, thickeners such as xanthan guma, preservatives, or an antigelling agent such as monopropylene glycol or monoethylene glycol.

As previously indicated the suspo-emulsion may be prepared from the various compounds of which it is composed. Preferably, the suspo-emulsion is prepared by mixing the aqueous suspension of active substance and the aqueous emulsion previously described.

The proportions of suspension and emulsion are such that the suspo-emulsion globally contains from 5% to 60% by weight of active substance relative to its total volume.

The proportions of suspension and emulsion are such that the suspo-emulsion contains from 0.1% to 12% by weight of a nonionic or anionic surface-active agent relative to its total volume.

The proportions of suspension and emulsion are such that the suspo-emulsion contains from 0.2% to 15% by weight of sucroglycerides relative to its total volume.

The proportions of suspension and emulsion are such that the suspo-emulsion contains from 0% to 6% by weight of phospholipid relative to its total volume.

The proportions of suspension and emulsion are such that the suspo-emulsion contains from 0.1% to 5% by weight of at least one compound selected from alkoxylated triglyceride, alkoxylated fatty acid, sorbitan ester and alkoxylated sorbitan ester relative to its total volume.

The proportions of suspension and emulsion are such that the suspo-emulsion contains from 0.05% to 0.7% by weight of wetting agent relative to its total volume.

The proportions of suspension and emulsion are such that the suspo-emulsion contains from 3% to 50% by weight of oil relative to its total volume.

The suspo-emulsions, in accordance with the present invention, are very stable over a wide range of temperatures such as between −10° C. and +54° C., and have the advantage of being filmogens, which ensures a good fixation and a good permanence of the active substance on the plants which are to be treated or on the parasites to be destroyed. The suspo-emulsion also possesses antifoaming ability due to the presence of sucroglycerides.

In the following illustrative examples of the invention, the quantities of the various constituents of the suspensions or emulsions are given in grams for obtaining 1,000 cm$^3$ of suspension or emulsion.

EXAMPLES OF PREPARATION OF SUSPENSIONS OF ACTIVE SUBSTANCE

The procedure used was the same for the different examples.

First, the melted sucroglycerides were dispersed by mixing in water at 60° C., at 10% by weight/weight.

This predispersion allowed the sucroglycerides to swell.

In the examples, the sucroglycerides were used in the form of a predispersion at 10% weight/weight in water.

The ethoxylated triglyceride or ethoxylated fatty acid and the wetting agent were dissolved in water. The predispersion of the sucroglycerides, and the antigelling compounds when desired, was then added.

The active substance was then added in small fractions with stirring as well as the antifoaming agent, when necessary.

The mixture was homogenized using a turbine, and then ground for some minutes in a ball mill (glass beads of a 1 mm in diameter) until an average particle size of 3 to 4 micrometers of the active substance was obtained. Changes in the diameter of the particles were monitored using a granulometer.

A thickener (xanthan gum) was added when necessary and mixing was continued for about 30 minutes.

Examples 1 to 4 and Comparative Test A

Preparation of aqueous suspensions of atrazine.

Atrazine is a known herbicide, which has a melting point of 175° C. and a solubility in water at 25° C. of 0.028 g/l:

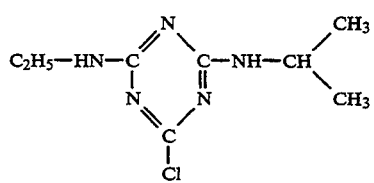

Following the procedure previously described, four aqueous suspensions of atrazine in accordance with the present invention, and an aqueous suspension of atrazine not containing an ethoxylated triglyceride (comparative test A) were prepared. The respective compositions are shown in Table 1 below.

Table 1 also shows for each of the suspensions:
the average diameter of particles of the active substance (in micrometers),
the value, in seconds, for the measurement of the flow rate of the suspension (before addition of the thickener: xanthan gum) using a No. 4 Ford Cup (FC No. 4),
the abbreviation EO corresponds to the oxyethylene unit in the formula for triglycerides or ethoxylated fatty acids.

The antifoam agent used was a polydiorgano-siloxane.

All the suspensions in Examples 1 to 4 were stable:
more than 2 months at 45° C. and
more than 2 months in the temperature cycle: 24 hours at +45° C., 24 hour at −5° C.

Dilution with water produced suspensions of 0.5% to 2% of active substance, without flocculation or sedimentation, during period of use of about 24 hours.

The suspension according to the comparative test was also stable to storage, but it was difficult to grind and flocculation was observed on dilution with water.

TABLE 1

| Constituents of the suspension | Example 1 | Example 2 | Example 3 | Example 4 | Test A |
|---|---|---|---|---|---|
| Atrazine | 500 g | 500 g | 500 g | 500 g | 500 g |
| Sucrogylcerides of castor oil at 10% in water | 150 g | 80 g | 100 g | 100 g | 150 g |
| Ethoxylated castor oil (about 33 EO) | 5 g | 4 g | 5 g | 5 g | 0 g |
| Ethoxylated copra oil (about 27 EO) | 0 g | 0 g | 0 g | 5 g | 0 g |
| Sodium dodecylbenzenesulphonate | 0 g | 2 g | 0 g | 0.5 g | 2 g |
| Sodium laurylsulphate | 2 g | 0 g | 2 g | 0 g | 0 g |
| Monopropylene glycol | 70 g | 80 g | 70 g | 70 g | 80 g |
| Xanthan gum, 2% in water | 50 g | 50 g | 50 g | 50 g | 50 g |
| Antifoaming agent | 1 g | 1 g | 1 g | 1 g | 1 g |
| Water (sufficient quantity for 1,000 cm³) | 300 g | 450 g | 349 g | 345 g | 295 g |
| Average diameter of particles (in micrometers) | 3.1 | 3.1 | 2.8 | 3.2 | — |
| FC No. 4 | 17 s | 15 s | 35 s | 22 s | — |

Examples 5 to 8

Preparation of aqueous suspensions of atrazine.

Following the procedure previously described, four aqueous suspensions of atrazine, whose respective compositions and properties are shown in Table 2 below (with the same abbreviations as in Table 1), were prepared.

As with the suspensions in Examples 1 to 4, all the suspensions in Examples 5 to 8 were stable:
more than 2 months at 45° C. and
more than 2 months in the temperature cycle: 24 hours at +45° C., 24 hour at −5° C.

By diluting with water, suspensions were produced with 0.5% to 2% of active substance, without flocculation or sedimentation, during a period of use of about 24 hours.

TABLE 2

| Constituents of the suspension | Example 5 | Example 6 | Example 7 | Example 8 |
|---|---|---|---|---|
| Atrazine | 500 g | 500 g | 500 g | 350 g |
| Sucrogylcerides of tallow at 10% in water | 100 g | 50 g | 80 g | 50 g |
| Ethoxylated castor oil (about 33 EO) | 5 g | 4 g | 0 g | 5 g |
| Ethoxylated castor oil (about 18 EO) | 0 g | 0 g | 8 g | 0 g |
| Ethoxylated copra oil (about 27 EO) | 0 g | 0 g | 8 g | 0 g |
| Sodium dodecylbenzenesulphonate | 0 g | 2 g | 2 g | 0 g |
| Sodium laurylsulphate | 2 g | 0 g | 0 g | 2 g |
| Monopropylene glycol | 80 g | 80 g | 80 g | 80 g |
| Xanthan gum, at 2% in water | 50 g | 50 g | 40 g | 60 g |
| Antifoaming agent | 1 g | 1 g | 1 g | 1 g |
| Water (sufficient quantity for | 338 g | 388 g | 354 g | 505 g |

TABLE 2-continued

| Constituents of the suspension | Example 5 | Example 6 | Example 7 | Example 8 |
|---|---|---|---|---|
| 1,000 cm$^3$) | | | | |
| Average diameter of particles (in micrometers) | 2.8 | 3.1 | 3.4 | 3.2 |
| FC No. 4 | 33 s | 20 s | 40 s | 10 s |

Examples 9 to 11

Preparation of aqueous suspensions of atrazine.

Following the procedure previously described, three aqueous suspensions of atrazine, whose respective compositions and properties are shown in Table 3 below (with the same abbreviations as in Table 1), were prepared.

As with the suspension in Examples 1 to 4, all the suspensions in Examples 9 to 11 were stable:
more than 2 months at 45° C. and
more than 2 months in the temperature cycle: 24 hours at +45° C., 24 hours at −5° C.

By diluting with water, suspensions were produced with 0.5% to 2% of active substance, without flocculation or sedimentation, during a period of use of about 24 hours.

TABLE 3

| Constituents of the suspension | Example 9 | Example 10 | Example 11 |
|---|---|---|---|
| Atrazine | 500 g | 450 g | 500 g |
| Sucroglycerides of copra at 10% in water | 100 g | 0 g | 0 g |
| Sucrogylcerides of butter at 10% in water | 0 g | 100 g | 0 g |
| Sucroglcerides of tallow at 10% in water | 0 g | 0 g | 250 g |
| Ethoxylated castor oil (about 33 EO) | 5 g | 5 g | 5 g |
| Sodium dodecylbenzenesulphonate | 2 g | 2 g | 2 g |
| Monopropylene glycol | 80 g | 80 g | 60 g |
| Xanthan gum, 2% in water | 50 g | 50 g | 50 g |
| Antifoaming agent | 1 g | 1 g | 1 g |
| Water (sufficient quantity for 1,000 cm$^3$) | 338 g | 380 g | 208 g |
| Average diameter of particles (in micrometers) | 3.0 | 3.3 | 3.5 |
| FC No. 4 | 20 s | 15 s | 17 s |

Examples 12 to 15

Preparation of aqueous suspensions of diuron.

Diuron is a known herbicide, with a melting point of 158° C. and a solubility in water at 25° C. of 0.042 g/l:

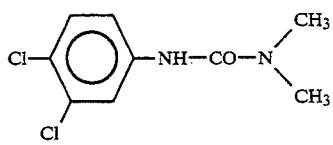

Following the procedure previously described, four aqueous suspensions of diuron, whose respective compositions are shown in Table 4 below (with the same abbreviations as in Table 1), were prepared in accordance with the invention.

As with the suspensions in Examples 1 to 4, all the suspensions in Examples 12 to 15 were stable:
more than 2 months at 45° C. and
more than 2 months in the temperature cycle: 24 hours at +45° C., 24 hours at −5° C.

By diluting with water, suspensions were produced with 0.5% to 2% of active substance, without flocculation or sedimentation, during a period of use of about 24 hours.

TABLE 4

| Constituents of the suspension | Example 12 | Example 13 | Example 14 | Example 15 |
|---|---|---|---|---|
| Diuron | 600 g | 600 g | 600 g | 550 g |
| Sucrogylcerides of castor oil at 10% in water | 100 g | 150 g | 150 g | 100 g |
| Ethoxylated castor oil (about 33 EO) | 5 g | 8 g | 11 g | 5 g |
| Ethoxypropoxylated nonylphenol | 0 g | 0 g | 0 g | 2 g |
| Ethoxylated nonylphenol (about 12 EO) | 0 g | 3 g | 0 g | 0 g |
| Ethoxylated nonylphenol (about 8 EO) | 5 g | 0 g | 0 g | 0 g |
| Ethoxylated nonylphenol (about 1 EO) | 0 g | 0 g | 3 g | 3 g |
| Dioctyl sodium sulphosuccinate | 0 g | 0 g | 1 g | 0 g |
| Monopropylene glycol | 70 g | 70 g | 70 g | 70 g |
| Xanthan gum, at 2% in water | 50 g | 50 g | 50 g | 50 g |
| Antifoaming agent | 1 g | 1 g | 1 g | 1 g |
| Water (sufficient quantity for 1,000 cm$^3$) | 370 g | 318 g | 314 g | 402 g |
| Average diameter of particles (in micrometers) | 3.8 | 3.7 | 3.5 | 3.3 |
| FC No. 4 | 35 s | 30 s | 28 s | 27 s |

Examples 16 to 20

Preparation of aqueous suspensions of diuron.

Following the procedure previously described, five aqueous suspensions of diuron, whose respective compositions are shown in Table 5 below (with the same abbreviations as in Table 1), were prepared in accordance with the invention.

As with the suspensions in Examples 1 to 4, all the suspensions in Examples 16 to 20 were stable:
more than 2 months at 45° C. and
more than 2 months in the temperature cycle: 24 hours at +45° C., 24 hours at −5° C.

By diluting with water, suspensions were produced of 0.5% to 2% of active substance, without flocculation or sedimentation, during a period of use of about 24 hours.

TABLE 5

| Constituents of the suspension | Example 16 | Example 17 | Example 18 | Example 19 | Example 20 |
|---|---|---|---|---|---|
| Diuron | 600 g | 580 g | 640 g | 640 g | 640 g |
| Sucrogylcerides of copra oil at 10% in water | 150 g | 145 g | 140 g | 140 g | 140 g |
| Ethoxylated castor oil (about 33 EO) | 5 g | 0 g | 0 g | 5 g | 5 g |
| Ethoxylated castor oil (about 18 EO) | 0 g | 5 g | 5 g | 0 g | 0 g |
| Ethoxylated nonylphenol (about 10 EO) | 5 g | 3 g | 4 g | 5 g | 3 g |
| Ethoxylated $C_{11}$ fatty acid in (about 7 EO) | 0 g | 0 g | 0 g | 0 g | 5 g |
| Sodium dodecylbenzensulphonate | 3 g | 3 g | 2 g | 0 g | 0 g |
| Dioctyl sodium sulphosuccinate | 0 g | 0 g | 0 g | 2 g | 0 g |
| Monopropylene glycol | 70 g | 70 g | 60 g | 60 g | 60 g |
| Xanthan gum, 2% in water | 50 g | 50 g | 40 g | 40 g | 40 g |
| Antifoaming agent | 1 g | 1 g | 1 g | 1 g | 1 g |
| Water (sufficient quantity for 1,000 $cm^3$) | 316 g | 336 g | 321 g | 320 g | 319 g |
| Average diameter of particles (in micrometers) | 3.5 | 3.6 | 3.8 | 3.7 | 3.5 |
| FC No. 4 | 30 s | 35 s | 40 s | 40 s | 38 s |

Examples 21 and 22

Preparation of aqueous suspensions of diuron.

Following the procedure previously described, two aqueous suspensions of diuron, whose respective compositions are shown in Table 6 below (with the same abbreviations as in Table 1), were prepared in accordance with the invention.

As with the suspensions in Examples 1 to 4, all the suspensions in Examples 21 to 22 were stable=
more than 2 months at 45° C. and
more than 2 months in the temperature cycle: 24 hours at +45° C., 24 hours at −5° C.

By diluting with water, suspensions were produced with 0.5% to 2% of active substance, without flocculation or sedimentation, during a period of use of about 24 hours.

TABLE 6

| Constituents of the suspension | Example 21 | Example 22 |
|---|---|---|
| Diuron | 430 g | 450 g |
| Sucroglycerides of copra oil at 10% in water | 120 g | 0 g |
| Sucroglycerides of butter oil at 10% in water | 0 g | 100 g |
| Ethoxylated castor oil (about 33 EO) | 5 g | 10 g |
| Ethoxylated castor oil (about 18 EO) | 5 g | 0 g |
| Sodium dodecylbenzenesulphonate | 5 g | 5 g |
| Monopropylene glycol | 70 g | 70 g |
| Xanthan gum, 2% in water | 60 g | 60 g |
| Antifoaming agent | 1 g | 1 g |
| Water (sufficient quantity for 1,000 $cm^3$) | 447 g | 455 g |
| Average diameter of particles (in micrometers) | 3.2 | 3.5 |
| FC No. 4 | 10 s | 12 s |

Examples 23 and 24

Preparation of aqueous suspensions of triflumizole.

Triflumizole is a known fungicide, with a melting point of 63° C. and a solubility in water at 25° C. of 0.012 g/l:

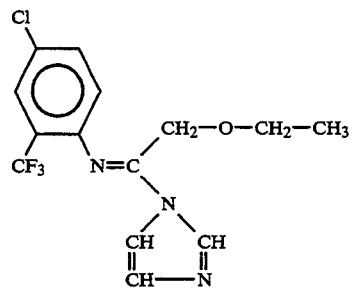

Following the procedure previously described, two aqueous suspensions of triflumizole, whose respective compositions are shown in Table 7 below (with the same abbreviations as for Table 1) were prepared in accordance with the invention.

As with the suspensions in Example 1 to 4, all the suspensions in Examples 23 and 24 were stable:
for more than 2 months at a temperature lower than 35° C. (maximum temperature for the stability of the active substance).

By diluting with water, suspensions were produced of 0.5% to 2% of active substance, without flocculation or sedimentation, during a period of use of about 24 hours.

TABLE 7

| Constituents of the suspension | Example 23 | Example 24 |
|---|---|---|
| Triflumizole | 430 g | 500 g |
| Sucroglycerides of tallow at 10% in water | 130 g | 0 g |
| Sucroglycerides of castor oil (about 33 EO) | 0 g | 200 g |
| Ethoxylated castor oil (about 33 EO) | 8 g | 20 g |
| Sodium dodecylbenzenesulphonate | 3 g | 0 g |
| Sodium laurylsulphate | 0 g | 3 g |
| Monopropylene glycol | 60 g | 70 g |
| Xanthan gum, 2% in water | 50 g | 50 g |
| Antifoaming agent | 1 g | 1 g |
| Water (sufficient quantity for 1,000 $cm^3$) | 374 g | 220 g |
| Average diameter of particles (in micrometers) | 4.2 | 4.5 |
| FC No. 4 | 39 s | 46 s |

Example 25

Preparation of 1,000 $cm^3$ of aqueous suspension of isoproturon.

60 g of monopropylene glycol, 20 g of sodium methylnaphthalenesulphonate condensed with formaldehyde and 5 g of ethoxylated nonylphenol (10 EO) were mixed.

650 g of isoproturon, 436 g of water and 5 g of polydiorganosiloxane antifoaming agent were slowly added with stirring.

The predispersion was ground in a ball mill (glass beads of a diameter of one nun; 4,000 revolutions/minute) until an average particle size of the active substance of 5 micrometers was obtained. The evolution in the diameter of the particle was monitored using a granulometer.

The flow rate of the suspension using the No. 4 Ford Cup was 19 s.

Example 26

Preparation of 1,000 cm³ of aqueous suspension of atrazine 60 g of monopropylene glycol, 35 g of phosphoric esters (mono- and di-) of ethoxylated tristyrylphenol (16 EO) neutralized with triethanolamine and 5 g of ethoxylated nonylphenol (10 EO) were mixed.

600 g of atrazine, 390 g of water and 5 g of polydiorganosiloxane antifoaming agent were slowly added with stirring.

The predispersion was ground in a ball mill (glass beads of a diameter of one mm; 4,000 revolutions/minute) until an average particle size of the active substance of 3.5 micrometers was obtained. The evolution in the diameter of the particles was monitored using a granulometer.

The flow rate of the suspension using the No. 4 Ford Cup was 22 s.

EXAMPLES OF PREPARATION OF EMULSIONS

Example 27

To 560 g of colza oil were added:
18.65 g of sucroglycerides of colza oil
18.65 g of ethoxylated copra oil (about 27 EO)
18.65 g of ethoxylated castor oil (about 18 EO).

The mixture was homogenized and then slowly poured into 295 g of a water/monopropylene glycol mixture (83.4% and 16.6% by weight/weight respectively) with stirring (800 revolutions/min).

An oil in water emulsion was obtained.

The emulsion was then homogenized using a turbine at 8,000 revolution/min for about 3 min.

A stable oil-in-water emulsion having the following characteristics was obtained:
average size 1.31 micrometers,
viscosity 500 mPa.s.

The emulsion was stabilized by adding 30 g of a 2% solution of xanthan gum.

1,000 cm³ of an aqueous emulsion having the following composition were thus obtained:

| | |
|---|---|
| colza oil | 560 g |
| sucroglycerides of colza oil | 18.65 g |
| ethoxylated copra oil (about 27 EO) | 18.65 g |
| ethoxylated castor oil (about 18 EO) | 18.65 g |
| monopropylene glycol | 49 g |
| xanthan gum at 2% in water | 30 g |
| water | 246 g |
| The emulsion was stable: | |
| more than 2 months at 45° C. and | |
| more than 2 months in the temperature cycle: | |
| 24 hours at +45° C., 24 hours at −5° C. | |

The emulsion was stable:
more than 2 months at 45° C. and
more than 2 months in the temperature cycle: 24 hours at +45° C., 24 hours at −5° C.

Examples 28 to 31

The sucroglyceride of castor oil, followed by colza oil, or a colza oil/sucroglycerides of colza oil mixture or a colza oil/crude soybean lecithin mixture were slowly poured, with stirring (800 revolutions/min), into a water/monopropylene glycol mixture (83.4% and 16.6%, by weight/weight respectively).

An oil-in-water emulsion was obtained.

The emulsion was then homogenized using a turbine at 8,000 revolution/min for about 3 min, and was stabilized by adding 30 g of a 2% solution of xanthan gum.

1,000 cm³ of a stable oil-in-water emulsion, whose characteristic are shown in Table 8 below, was obtained (the viscosity was measured before the addition of the xanthan gum).

The emulsion was stable:
more than 2 months at 45° C. and
more than 2 months in the temperature cycle: 24 hours at +45° C., 24 hours at −5° C.

TABLE 8

| Constituents of the emulsion | Example 28 | Example 29 | Example 30 | Example 31 |
|---|---|---|---|---|
| Colza oil | 560 g | 560 g | 560 g | 560 g |
| Sucrogylcerides of castor oil | 56 g | 28 g | 14 g | 14 g |
| Sucroglycerides of colza oil | 0 g | 28 g | 14 g | 0 g |
| Crude soybean lecithin | 0 g | 0 g | 0 g | 14 g |
| Monopropylene glycol | 49 g | 49 g | 52 g | 52 g |
| Xanthan gum at 2% in water | 30 g | 30 g | 30 g | 30 g |
| Water (sufficient quantity for 1,000 cm³) | 246 g | 246 g | 268 g | 268 g |
| Average size (in micrometers) | 1.98 | 1.59 | 2.57 | 2.36 |
| Viscosity (in mPa.s) | 660 | 975 | 570 | 970 |

Examples 32 and 33

To 380 g of colza oil were added 26.6 g of either sucroglycerides of tallow, or sucroglycerides of colza oil and 11.4 g of crude soybean lecithin.

The mixture was homogenized. The following were then slowly poured into the mixture:
342 g of a water/monopropylene glycol mixture (82.35% and 17.65% by weight/weight respectively) with stirring (800 revolutions/min),
then 167.3 g of water with strong stirring (8,000 revolutions/min).

The emulsion of Example 32 was stabilized by adding 30 g of a 2% solution of xanthan guan.

1,000 cm³ of a table oil in water emulsion, whose characteristics are shown in Table 9 below, was obtained (the viscosity was measured before the addition of the xanthan gum).

Each emulsion was stable:

more than 2 months at 45° C. and
more than 2 months in the temperature cycle: 24 hours at +45° C., 24 hours at −5° C.

TABLE 9

| Constituents of the suspension | Example 32 | Example 33 |
|---|---|---|
| Colza oil | 380 g | 380 g |
| Sucroglycerides of tallow | 26.6 g | 0 g |
| Sucroglycerides of colza oil | 0 g | 26.6 g |
| Crude soybean lecithin | 11.4 g | 11.4 g |
| Monopropylene glycol | 60.4 g | 60.4 g |
| Xanthan gum at 2% in water | 30 g | 0 g |
| Water (sufficient quantity for 1,000 cm³) | 449 g | 479 g |
| Average size (in micrometers) | 2.45 | 2.3 |
| Viscosity (in mPa.s) | 90 | 75 |

Example 34

Into 560 g of soybean oil were introduced:
18.65 g of sucroglycerides of colza oil
18.65 g of ethoxylated copra oil (about 27 EO)
18.65 g of ethoxylated castor oil (about 18 EO).

The mixture was homogenized, and then slowly poured into 295 g of a water/monopropylene glycol mixture (83.4% and 16.6% by weight/weight respectively) with stirring (800 revolutions/min).

An oil in water emulsion was obtained.

The emulsion was then homogenized using a turbine at 8,000 revolutions/min for about 3 min.

A stable oil in water emulsion which has the following characteristics was obtained:
average size 1.30 micrometers,
viscosity 500 mPa.s The emulsion was stabilized by adding 30 g of a 2% solution of xanthan gum.

1,000 cm³ of an aqueous emulsion having the following composition was thus obtained:

| | |
|---|---|
| soybean oil | 560 g |
| sucroglycerides of colza oil | 18.65 g |
| ethoxylated copra oil (about 27 EO) | 18.65 g |
| ethoxylated castor oil (about 18 EO) | 18.65 g |
| monopropylene glycol | 49 g |
| xanthan gum at 2% in water | 30 g |
| water | 246 g |

The emulsion was stable:
more than 2 months at 45° C. and
more than 2 months in the temperature cycle: 24 hours at +45° C., 24 hours at −5° C.

The emulsion was stable:
more than 2 months at 45° C. and
more than 2 months in the temperature cycle: 24 hours at +45° C., 24 hours at −5° C.

Examples 35 to 70

Preparation of suspo-emulsions using the aqueous suspensions and aqueous emulsions from the preceding examples.

Using, respectively, an aqueous suspension and an aqueous emulsion obtained in the preceding examples, various suspo-emulsions were prepared by simple mixing.

The relative volume of the suspension and emulsion are shown in Table 10 below.

Each suspo-emulsion obtained was stable:
more than 2 months at 45° C. and
more than 2 months in the temperature cycle: 24 hours at +45° C., 24 hours at −5° C.

TABLE 10

| SUSPO-EMULSION | SUSPENSION USED | EMULSION USED |
|---|---|---|
| Example 35 | 50 cm³ of Example 25 | 50 cm of Example 28 |
| Example 36 | 50 cm³ of Example 25 | 100 cm³ of Example 28 |
| Example 37 | 100 cm³ of Example 25 | 50 cm³ of Example 28 |
| Example 38 | 50 cm³ of Example 25 | 50 cm³ of Example 31 |
| Example 39 | 50 cm³ of Example 25 | 100 cm³ of Example 31 |
| Example 40 | 100 cm³ of Example 25 | 50 cm³ of Example 31 |
| Example 41 | 50 cm³ of Example 26 | 50 cm³ of Example 27 |
| Example 42 | 50 cm³ of Example 26 | 100 cm³ of Example 27 |
| Example 43 | 100 cm³ of Example 26 | 50 cm³ of Example 27 |
| Example 44 | 50 cm³ of Example 26 | 50 cm³ of Example 32 |
| Example 45 | 50 cm³ of Example 26 | 100 cm³ of Example 32 |
| Example 46 | 100 cm³ of Example 26 | 50 cm³ of Example 32 |
| Example 47 | 50 cm³ of Example 1 | 50 cm³ of Example 28 |
| Example 48 | 50 cm³ of Example 1 | 100 cm³ of Example 28 |
| Example 49 | 100 cm³ of Example 1 | 50 cm³ of Example 28 |
| Example 50 | 50 cm³ of Example 1 | 50 cm³ of Example 31 |
| Example 51 | 50 cm³ of Example 1 | 100 cm³ of Example 31 |
| Example 52 | 100 cm³ of Example 1 | 50 cm³ of Example 31 |
| Example 53 | 50 cm³ of Example 9 | 50 cm³ of Example 29 |
| Example 54 | 50 cm³ of Example 9 | 100 cm³ of Example 29 |
| Example 55 | 100 cm³ of Example 9 | 50 cm³ of Example 29 |
| Example 56 | 50 cm³ of Example 9 | 50 cm³ of Example 30 |
| Example 57 | 50 cm³ of Example 9 | 100 cm³ of Example 30 |
| Example 58 | 100 cm³ of Example 9 | 50 cm³ of Example 30 |
| Example 59 | 50 cm³ of Example 15 | 50 cm³ of Example 28 |
| Example 60 | 50 cm³ of Example 15 | 100 cm³ of Example 28 |
| Example 61 | 100 cm³ of Example 15 | 50 cm³ of Example 28 |
| Example 62 | 50 cm³ of Example 15 | 50 cm³ of Example 31 |
| Example 63 | 50 cm³ of Example 15 | 100 cm³ of Example 31 |
| Example 64 | 100 cm³ of Example 15 | 50 cm³ of Example 31 |
| Example 65 | 50 cm³ of Example 21 | 50 cm³ of Example 32 |
| Example 66 | 50 cm³ of Example 21 | 100 cm³ of Example 32 |
| Example 67 | 100 cm³ of Example 21 | 50 cm³ of Example 32 |
| Example 68 | 50 cm³ of Example 21 | 50 cm³ of Example 27 |
| Example 69 | 50 cm³ of Example 21 | 100 cm³ of Example 27 |
| Example 70 | 100 cm³ of Example 21 | 50 cm³ of Example 27 |

What is claimed is:

1. A suspo-emulsion of a solid active plant-protection substance, comprising:
at least one oil; a first surface-active system containing at least sucroglycerides; a solid active plant-protection substance; and either (A) a nonionic or artionic surface-active agent, or (B) a second surface-active system containing sucroglycerides and at least one compound selected from the group consisting of an alkoxylated triglyceride, an alkoxylated fatty acid, a sorbitan ester, and an alkoxylated sorbitan ester,
wherein said solid active plant-protection substance has a melting point greater than or equal to 45° C. and is substantially insoluble in water.

2. The suspo-emulsion according to claim 1, wherein said suspo-emulsion is a mixture of:
an aqueous emulsion of said at least one oil and said first surface-active system containing at least sucroglycerides,
and an aqueous suspension of said solid active plant-protection substance and either (A) or (B).

3. The suspo-emulsion according to claim 2, wherein said aqueous suspension further contains a wetting agent.

4. The suspo-emulsion according to claim 1, wherein the sucroglyceride is prepared by transesterification of triglycerides with saccharose.

5. The suspo-emulsion according to claim 4, wherein the triglycerides are natural and are selected from the group consisting of lard, tallow, groundnut oil, butter oil, cotton-seed oil, linseed oil, olive oil, palm oil, grape-seed oil, fish oil, soybean oil, castor oil, colza oil, copra oil and coconut oil.

6. The suspo-emulsion according to claim 1, wherein the sucroglycerides used are obtained from palm oil, lard, copra oil, tallow, colza oil or castor oil.

7. The suspo-emulsion according to claim 2, wherein the aqueous emulsion further contains a phospholipid selected from the group consisting of crude lecithins of plant or animal origin and lecithin fractions.

8. The suspo-emulsion according to claim 7, wherein said crude lecithins are soybean lecithins or egg-yolk lecithins.

9. The suspo-emulsion according to claim 1, wherein the oil is selected from the group consisting of colza oil, sunflower oil, palm oil, groundnut oil, linseed oil, copra oil, grape-seed oil, nut oil, fish oil, and methyl oleate.

10. The suspo-emulsion according to claim 9, wherein said oil is selected from the group consisting of colza oil, sunflower oil, soybean oil and methyl oleate.

11. The suspo-emulsion according to claim 2, wherein the aqueous emulsion contains, by weight relative to the total volume of the emulsion:
from 0.2% to 15% of sucroglycerides, and
from 5% to 70% of oil, and further comprises from 0% to 8% of phospholipid.

12. The suspo-emulsion according to claim 11, wherein the aqueous emulsion contains, by weight relative to the total volume of the emulsion:
from 0.5% to 10% of sucroglycerides,
from 0% to 5% of phospholipid,
from 10% to 60% of oil, 13. The suspo-emulsion according to claim 2, wherein the aqueous emulsion further contains at least one compound selected from the group consisting of alkoxylated triglycerides, alkoxylated fatty acids, sorbitan esters and alkoxylated sorbitan esters.

14. The suspo-emulsion according to claim 13, wherein said at least one compound is selected from the group consisting of ethoxylated triglycerides, ethoxylated fatty acids, or fatty acid esters sorbitan esters and ethoxylated sorbitan esters.

15. The suspo-emulsion according to claim 14, wherein the ethoxylated triglycerides are ethoxylated triglycerides of plant or animal origin.

16. The suspo-emulsion according to claim 15, wherein the ethoxylated triglycerides of plant or animal origin are selected from the group consisting of lard, tallow, groundnut oil, butter oil, cotton-seed oil, linseed oil, olive oil, palm oil, grape-seed oil, fish oil, soybean oil, castor oil, colza oil, copra oil and coconut oil.

17. The suspo-emulsion according to claim 14, wherein the compound is selected from ethoxylated fatty acid esters.

18. The suspo-emulsion according to claim 17, wherein the ethoxylated fatty acid esters are oleic acid or stearic acid.

19. The suspo-emulsion according to claim 14, wherein the sorbitan esters are cyclic sorbitol esters of fatty acids from $C_{10}$ to $C_{20}$.

20. The suspo-emulsion according to claim 19, wherein the cyclic sorbitol esters of fatty acids are lauric acid, stearic acid or oleic acid.

21. The suspo-emulsion according to claim 2, wherein the aqueous emulsion further contains from 0 to 10% by weight of at least one compound selected from the group consisting of alkoxylated triglycerides, alkoxylated fatty acids, sorbitan esters, and alkoxylated sorbitan esters, per total volume of the emulsion.

22. The suspo-emulsion according to claim 21, wherein the aqueous emulsion contains from 0.2% to 6% by weight, of said at least one compound selected from the group consisting of alkoxylated triglycerides, alkoxylated fatty acids, sorbitan esters and alkoxylated sorbitan esters per total volume of the emulsion.

23. The suspo-emulsion according to claim 1, wherein the solid active plant-protection substance is selected from the group consisting of deltamethrin, propham, tetramethrin, furalaxyl, heptachlor, propanil, oxadiazon, triflumizole, dimethamethrin, atrazine, diuron, neburon, linuron, isoproturon, simazine, ametryne, phenmedipham, and pendimethalin.

24. The suspo-emulsion according to claim 2, wherein the aqueous suspension of solid active plant-protection substance contains a nonionic surface-active agent selected from the group consisting of alkoxylated di(1-phenylethyl)-phenols, alkoxylated tri(1-phenylethyl)-phenols, alkoxylated alkylphenols, alkoxylated fatty amines, alkoxylated fatty alcohols, alkoxylated castor oils, and polymers of the sequence ethylene oxide-propylene oxide (EO-PO) or ethylene oxide-propylene oxide-ethylene oxide (EO-PO-EO).

25. The suspo-emulsion according to claim 24, wherein the alkoxylated units of the surface-active agents are oxyethylene or oxypropylene units, wherein the number of said units varies from 2 to 100.

26. The suspo-emulsion according to claim 25, wherein said number varies from 4 to 50.

27. The suspo-emulsion according to claim 24, wherein the nonionic surface-active agent is selected from the group consisting of ethoxylated di(1-phenylethyl)phenol with 15 ethylene oxide (EO) units, ethoxylated tri(1-phenylethyl)phenol with 16 EO units, ethoxylated tri(1-phenylethyl)phenol with 25 EO units, ethoxylated tri(1-phenyl-ethyl)phenol with 40 EO units, ethoxypropoxylated tri(1-phenylethyl)phenols, ethoxypropoxylated nonylphenols, and trisequenced polymers EO-PO-EO.

28. The suspo-emulsion according to claim 1, wherein the aqueous suspension of solid active plant-protection substance contains an anionic surface-active agent selected from the group consisting of:
phosphoric esters of ethoxylated alkylphenols, ethoxylated di(1-phenylethyl)phenols, ethoxylated tri(1-phenylethyl)phenols, ethoxylated fatty alcohols;
sulphuric esters of ethoxylated alkylphenols, ethoxylated di(1-phenylethyl)phenols, ethoxylated tri(1-phenylethyl)phenols, ethoxylated fatty alcohols;
sulphonic esters of ethoxylated alkylphenols, ethoxylated di(1-phenylethyl)phenols, ethoxylated tri(1-phenylethyl)phenols;
the salts of polycarboxylic acids, the homo-and copolymers of polycarboxylic acids, copolymers of maleic anhydride and diisobutylene;
alkylnaphthalenesulphonates, poly(alkylnaphthalenesulphonates); and
dihydroxydiphenylsulphonates condensed with folmaldehyde.

29. The suspo-emulsion according to claim 28, wherein the anionic surface-active agent is selected from the group consisting of triethanolamine salts of mono- and diphosphoric esters of ethoxylated tri(1-phenylethyl)phenol with 16 EO units, the ethoxylated acid sulphate of di(1-phenylethyl)phenol with 11 EO units, the ethoxylated acid phosphate of nonylphenol with 9 EO units, sodium methylnaphtha-lenesulphonate, and the sodium salt of polyacrylic acid.

30. The suspo-emulsion according to claim 2, wherein the aqueous suspension of the solid active plant-protection substance contains from 5% to 90% by weight of said active substance, relative to the total volume of the suspension.

31. The suspo-emulsion according to claim 30, wherein the aqueous suspension of the solid active plant-protective substance contains from 10% to 85% by weight of said active substance, relative to the total volume of the suspension.

32. The suspo-emulsion according to claim 30, wherein the aqueous suspension of the solid active plant-protection substance contains from 0.2% to 15% by weight of nonionic or anionic surface-active agent, relative to the total volume of the aqueous suspension.

33. The suspo-emulsion according to claim 32, wherein the aqueous suspension of the solid active plant-protection substance contains from 0.5% to 10% by weight of said nonionic or anionic surface-active agent, relative to the total volume of the aqueous suspension.

34. The suspo-emulsion according to claim 30, wherein the aqueous suspension of the solid active plant-protection substance contains from 0.1% to 5% by weight of at least one compound selected from sucroglycerides and phopholipid, 0.1% to 3% by weight of alkoxylated triglyceride, alkoxylated fatty acid, sorbitan ester, and alkoxylated sorbitan ester and 0.05% to 1% by weight of a wetting agent relative to the total volume of the aqueous suspension.

35. The suspo-emulsion according to claim 34, wherein the aqueous suspension of the solid active plant-protection substance contains from 0.2% to 4% by weight of sucroglycerides and phospholipid, 0.2% to 2.8% by weight of at least one selected from an alkoxylated triglyceride, an alkoxylated fatty acid, a sorbitan ester, and an alkoxylated sorbitan ester and 0.1% to 0.8% by weight of wetting agent relative to the total volume of the aqueous suspension.

36. The suspo-emulsion according to claim 34, wherein the wetting agent is selected from the group consisting of anionic salts of surface-active agents, alkoxylated alcohols and alkoxylated alkylphenols represented by the following formulae:

 $R_1$-$SO_3$-M

 $R_2$-$SO_4$M

 $R_3$-(EO)$_n$-H

 $R_3$-(PO)$_n$-H

 $R_3$-(EO-PO)$_n$-H

 $R_4$-COONa where:
$R_1$ represents
an alkylphenyl radical,
an alkyl radical, or
a 1,2-bi(octyloxycarbonyl)ethyl,
$R_2$ represents
an alkyl radical,
an ethoxylated alkylphenol radical or
an ethoxylated alkyl radical,
$R_3$ represents
an alkylaryl radical, or
an alkyl radical having 8 to 20 carbon atom.
n is a number from 4 to 12,
$R_4$ represents an alkyl radical having 10 to 22 carbon atoms,
M represents Na, K, $NH_4$ or a triethanolammonium cation.

37. The suspo-emulsion according to claim 36, wherein $R_1$ is dodecylphenyl, dodecyl, or 1, 2 his (2-ethylhexyl-oxycarbonyl) ethyl.

38. The suspo-emulsion according to claim 36, wherein $R_2$ is dodecyl or ethoxylated nonylphenol with 2 to 50 EO units.

39. The suspo-emulsion according to claim 36, wherein $R_3$ is nonylphenyl, alkylnaphthyl or alkyl radicals having 10 to 14 carbon atoms.

40. The suspo-emulsion according to claim 34, wherein the wetting agent is selected from the group consisting of silicone-based surface-active agents.

41. The suspo-emulsion according to claim 40, wherein said silicone-based surface-active agents are copolymers of polydimethylsiloxane and either a homopolymer of ethylene glycol or copolymers of ethylene glycol and propylene glycol.

42. The suspo-emulsion according to claim 34, wherein the wetting agent is selected from the group consisting of fluorinated surface-active agents.

43. The suspo-emulsion according to claim 42, wherein said fluorinated surface-active agent is selected from the group consisting of compounds containing a linear perfluorocarbon chain and a hydrophilic region.

44. The suspo-emulsion according to claim 43, wherein said linear perfluorocarbon chain is hydrophobic or oleophobic, and said hydrophilic region contains an acidic or neutralized sulphonic group, a carboxylic group or an ethoxylated alcohol radical.

45. The suspo-emulsion according to claim 34, wherein the weight ratio of sucroglycerides to phospholipid in the aqueous suspension of active substance is 0 to 3.

46. The suspo-emulsion according to claim 1, wherein the proportions of aqueous suspension and aqueous emulsion are such that the suspo-emulsion contain from 5% to 60% by weight of solid active plant-protection substance, relative to its total volume.

47. The suspo-emulsion according to claim 1, wherein the proportions of suspension and emulsion are such that the suspo-emulsion contains from 0.1% to 12% by weight of nonionic and/or anionic surface-active agent relative to its total volume.

48. The suspo-emulsion according to claim 1, wherein the proportions of suspension and emulsion are such that the suspo-emulsion contains from 0.2% to 15% by weight of sucroglycerides relative to its total volume.

49. The suspo-emulsion according to claim 1, wherein the proportions of suspension and emulsion are such that the suspo-emulsion contain from 0% to 6% by weight of phospholipid relative to it total volume.

50. The suspo-emulsion according to claim 1, wherein the proportions of suspension and emulsion are such that the suspo-emulsion contains from 0.1% to 5% by weight of alkoxylated triglyceride, alkoxylated fatty acid, sorbitan ester, alkoxylated sorbitan ester relative to its total volume.

51. The suspo-emulsion according to claim 1, wherein the proportions of suspension and emulsion are such that the suspo-emulsion contains from 0.05% to 0.7% by weight of wetting agent relative to it total volume.

52. The suspo-emulsion according to claim 1, wherein the proportions of suspension and emulsion are such that the suspo-emulsion contains from 3% to 50% by weight of oil relative to its total volume.

* * * * *

UNITED STATES PATENT AND TRADEMARK OFFICE
CERTIFICATE OF CORRECTION

PATENT NO. : 5,362,707
DATED : November 08, 1994
INVENTOR(S) : Jean-Francois FIARD et al.

It is certified that error appears in the above-indentified patent and that said Letters Patent is hereby corrected as shown below:

Claim 1, column 16, line 41 change "artionic" to --anionic--.

Claim 14, column 17, line 38 after first occurrence of "esters" insert --,--.

Claim 31, column 19, line 6 change "plant-protective" to --plant-protection--.

Claim 36, column 19, line 67 change "atom." to --atoms,--.

Claim 37, column 20, line 6 change "his" to --bis--.

Signed and Sealed this

Twenty-third Day of May, 1995

Attest:

BRUCE LEHMAN

*Attesting Officer*     *Commissioner of Patents and Trademarks*